United States Patent
Sathiosatham et al.

(10) Patent No.: US 9,546,190 B2
(45) Date of Patent: Jan. 17, 2017

(54) PROCESS FOR THE PREPARATION OF PHOSPHONIC ACID MONOMERS

(71) Applicant: Rohm and Haas Company, Philadelphia, PA (US)

(72) Inventors: Muhunthan Sathiosatham, Collegeville, PA (US); Douglass Sevon, Lansdale, PA (US)

(73) Assignee: Rohm and Haas Company, Philadelphia, PA (US)

(*) Notice: Subject to any disclaimer, the term of this patent is extended or adjusted under 35 U.S.C. 154(b) by 0 days.

(21) Appl. No.: 14/648,541

(22) PCT Filed: Nov. 26, 2013

(86) PCT No.: PCT/US2013/071778
§ 371 (c)(1),
(2) Date: May 29, 2015

(87) PCT Pub. No.: WO2014/088872
PCT Pub. Date: Jun. 12, 2014

(65) Prior Publication Data
US 2015/0307529 A1    Oct. 29, 2015

Related U.S. Application Data

(60) Provisional application No. 61/733,438, filed on Dec. 5, 2012.

(51) Int. Cl.
*C07F 9/38* (2006.01)
*C08F 230/02* (2006.01)

(52) U.S. Cl.
CPC ........... *C07F 9/3826* (2013.01); *C07F 9/3808* (2013.01); *C08F 230/02* (2013.01)

(58) Field of Classification Search
CPC ...... C07F 9/3808; C07F 9/3826; C07F 230/02
See application file for complete search history.

(56) References Cited

U.S. PATENT DOCUMENTS

| 4,733,005 A | 3/1988 | Schmidt et al. |
| 6,072,076 A * | 6/2000 | Schmidt ............... C07C 67/08 560/205 |
| 6,710,161 B2 | 3/2004 | Bardman et al. |
| 2003/0023107 A1 | 1/2003 | Riondel et al. |
| 2010/0112362 A1 | 5/2010 | Craciun et al. |
| 2010/0240822 A1 | 9/2010 | Trezzi et al. |

FOREIGN PATENT DOCUMENTS

| EP | 0278029 A1 | 8/1988 | |
| JP | 2000007687 | * 1/2000 | ............... C07F 9/38 |
| JP | 2009242805 A | 10/2009 | |
| WO | WO2011050121 | * 4/2011 | ............... B82B 3/00 |

OTHER PUBLICATIONS

English translation of JP2000007687, Jan. 2000, pp. 1-10.*
Lomoschitz, et al, "Directing Alkyl Chain Ordering of Functional Phosphorus Coupling Agents on ZrO2", Langmuir 2011, 27, abstract.
Gaboyard, et al., "Seeded Semicontinuous Emulsion Copolymerization of Methyl Methacrylate, Butyl Acrylate, and Phosphonated Methacrylates: Kinetics and Morphology", Journal of Polymer Science: Part A Polymer Chemistry 2003, 41, p. 2469-2480.
Bressy-Brondino, et al., "Adhesive and Anticorrosive Properties of Poly(vinylidene fluoride) Powders Blended with Phosphonated Copolymers on Galvanized Steel Plates", Journal of Applied Polymer Science 2002, 83. p. 2277-2287.
Tracy, et al, "Commercial Synthesis of Monoalkyl Phosphates", Journal of Surfactants and Detergents 2002, vol. 5, No. 2, p. 169-170.
El Asri et al., J Poly Sci Part A: Poly Chem, vol. 46, 4794-4803 (2008).

* cited by examiner

*Primary Examiner* — Paul A Zucker
*Assistant Examiner* — Mark Luderer
(74) *Attorney, Agent, or Firm* — Edward L. Brant

(57) ABSTRACT

A simple, commercially viable process for the preparation of phosphonic acid monomers containing essentially no diester or inorganic phosphorous acid compounds is disclosed.

12 Claims, No Drawings

PROCESS FOR THE PREPARATION OF PHOSPHONIC ACID MONOMERS

CROSS-REFERENCE TO RELATED APPLICATIONS

This application claims priority from provisional application Ser. No. 61/733,438, filed Dec. 5, 2012, which is incorporated herein by reference in its entirety.

BACKGROUND OF THE INVENTION

The invention relates to a process for preparing phosphonic acid monomers.

Polymers containing phosphorus acid groups are useful in many applications including coatings and adhesives. The phosphorus acid groups provide improved adhesion of the polymer to metal substrates, form crosslinks in the presence of divalent metal ions, and promote adsorption of the polymer to pigment particles, such as titanium dioxide, to form composite particles. However, such monomers generally contain many undesirable impurities and/or by-products.

U.S. Pat. No. 6,710,161 discloses a phosphorous acid-containing monomer composition that is substantially free of certain phosphorus acid compounds. However, the monomer must be treated prior to use in order to remove the unwanted phosphorus acid compounds, and only then can it be polymerized with a comonomer to produce a polymer that can be used to prepare coatings.

It would be desirable to have a simple, direct process for the preparation of phosphonic acid monomers.

SUMMARY OF THE INVENTION

The invention is such a process comprising contacting methacrylic acid (MAA) with a phosphorus reactant of the formula:

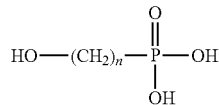

wherein n is a number having an average value of from 1 to 3, under reaction conditions sufficient to produce a product comprising a phosphonic acid compound of the formula:

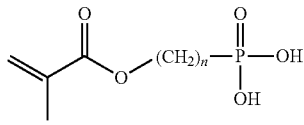

Surprisingly, the product monomer can be produced such that it is substantially free of inorganic phosphorous acid(s) and substantially free of diester cross-linkers, thereby avoiding the need for expensive and time-consuming purification steps for the removal of such compounds.

DETAILED DESCRIPTION OF THE INVENTION

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc.

Also herein, the recitations of numerical ranges and/or numerical values, including such recitations in the claims, can be read to include the term "about." In such instances the term "about" refers to numerical ranges and/or numerical values that are substantially the same as those recited herein.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent U.S. version is so incorporated by reference) especially with respect to the disclosure of definitions (to the extent not inconsistent with any definitions specifically provided in this disclosure) and general knowledge in the art.

Methacrylic acid (MAA) is well-known and widely commercially available.

In the process of the invention, MAA is reacted with a phosphorus reactant of formula I:

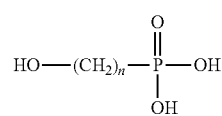

wherein n is a number having an average value of from 1 to 3. The amount of MAA employed advantageously is from 0.5 to 10 moles per mole of phosphorus reactant. In various embodiments of the invention, the amount of MAA employed is from 1 to 3 moles per mole of phosphorus reactant, or from 1.5 to 2 moles per mole of phosphorus reactant. Mixtures of phosphorus reactant can be employed.

The MAA and phosphorus reactant are contacted under reaction conditions sufficient to produce a phosphonic acid monomer of formula II:

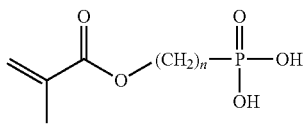

In one embodiment of the invention, the reactants are contacted under reduced pressure at elevated temperature for a time sufficient to produce the desired monomer. Advantageously, the temperature is from 70 to 170° C. and will depend, as known to those skilled in the art, on the pressure employed, the stage of the process, and the composition of the reaction mixture. Preferably the process temperature is from 90 to 150° C., and more preferably is from 120 to 140° C. Water is a by-product of the reaction and advantageously is removed as it vaporizes or boils out of the reaction mixture. The pressure advantageously is from 0 to 760 mmHg, and preferably is from 200 to 600 mmHg and more preferably is from 450 to 550 mmHg.

A polymerization inhibitor advantageously is employed in the process. The inhibitor is employed in an amount sufficient to prevent unwanted polymerization. Many inhibitors, and methods of their use, are known to those skilled in the art, and many inhibitors are commercially available. Examples of inhibitors include phenothiazine (PTZ), 4-hydroxy-TEMPO (4-HT), methoxy hydroquinone (MeHQ) and hydroquinone (HQ).

Advantageously, the reaction requires no additional solvent or catalyst, and produces the desired product in high yield. The process does not require expensive reagents, such as $(CH_3)_3SiBr$.

SPECIFIC EMBODIMENTS OF THE INVENTION

Example 1

Preparation of (methacroyloxy)ethyl phosphonic acid

A four-neck, 1000 ml round bottom flask equipped with an overhead stirrer, thermocouple and 10-tray distillation column is charged with 2-hydroxyethylphosphonic acid (125 g, 0.991 mol), methacrylic acid (180 g, 2.1 mol) and 45 mg of phenothiazine. The stirrer is turned on and set at 200 rpm, and the pressure of the reactor is set at 488 mmHg. Contents of the flask are heated to 130° C. over 45 minutes. Distillate begins to come off when the pot temperature reaches 125° C. and the vapor temperature stays between 80 to 90° C. After an hour, the vapor temperature begins to drop. The heat is turned off, and the vacuum is released. A sample is taken and analyzed by $^1$H-NMR and $^{31}$P-NMR spectroscopy. The NMR results indicate that 16% of the starting alcohol remains in the sample. The pressure of the reactor is reduced to 490 mmHg again and the contents are heated to 140° C. Distillate is collected at the vapor temperature range of 60-85° C. for an additional hour.

The remaining MAA is removed under full vacuum (<10 mmHg) at a pot temperature of 100 to 120° C. The product weighs 174 g (89% of the theoretical yield) and is analyzed by $^1$H, $^{13}$C, $^{31}$P-NMR spectroscopy. The results are consistent with the expected structure of a monomer with formula III, (methacroyloxy)ethyl phosphonic acid.

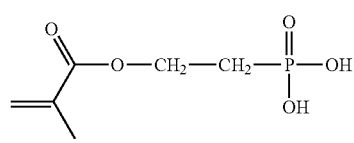

III

For some applications, it is not necessary to remove the remaining MAA, as the unseparated mixture can be used for polymerization.

Example 2

Preparation of (methacroyloxy)methyl phosphonic acid

A four-neck, 250 ml round bottom flask equipped with an overhead stirrer, thermocouple and 10-tray distillation column is charged with 2-hydroxymethylphosphonic acid (42 g, 0.38 mol), methacrylic acid (93 g, 1.1 mol) and 45 mg of phenothiazine. The stirrer is turned on and set at 200 rpm, and the pressure of the reactor is set at 497 mmHg. The contents of the flask are heated to 130° C. over 45 minutes. Distillate begins to come off when the pot temperature reaches 125° C. and the vapor temperature stays between 80 to 90° C. After two hours, the pressure is reduced to full vacuum (<10 mmHg), and the remaining MAA is removed at a pot temperature of 100 to 120° C. The product weighs 57 g (84% of the theoretical yield) and is analyzed by $^1$H, $^{31}$P-NMR spectroscopy. The results are consistent with the expected structure of a monomer with formula IV, (methacroyloxy)methyl phosphonic acid.

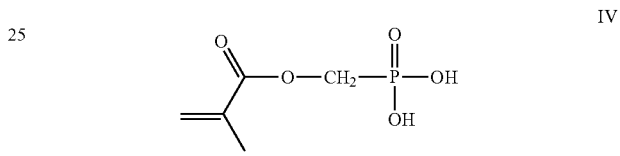

IV

What is claimed is:

1. A process comprising contacting methacrylic acid (MAA) with one or more phosphorus reactants of the formula:

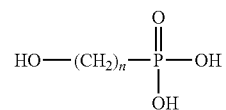

wherein n is a number having an average value of from 1 to 3, under reaction conditions sufficient to produce a product comprising a phosphonic acid compound of the formula:

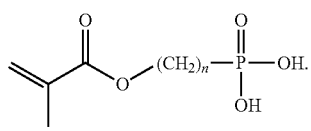

wherein the reaction is conducted in the substantial absence of added solvent and catalyst.

2. The process of claim 1 wherein the contacting is conducted in the presence of a polymerization inhibitor.

3. The process of claim 1 wherein the contacting is conducted in the temperature range of 70 to 170° C.

4. The process of claim 1 wherein the contacting is conducted in the temperature range of 130 to 140° C.

5. The process of claim 1 wherein the contacting is conducted in the pressure range of 0 to 760 mmHg.

6. The process of claim 1 wherein the contacting is conducted in the pressure range of 450 to 550 mmHg.

7. The process of claim 1 wherein from 0.5 to 10 moles of MAA is employed per mole of phosphorus reactant.

8. The process of claim 1 wherein the MAA is employed in the range of 1 to 3 moles per mole of phosphorus reactant.

9. The process of claim 1 wherein the MAA is employed in the range of 1.5 to 2 moles per mole of phosphorus reactant.

10. The process of claim 1 wherein the inhibitor is selected from the group consisting of phenothiazine, 4-hydroxy-TEMPO, methoxy hydroquinone, and hydroquinone.

11. The process of claim 1 wherein the product is substantially free of inorganic phosphorous acids.

12. The process of claim 1 wherein the product is substantially free of diester cross-linkers.

* * * * *